United States Patent [19]

Prugh

[11] Patent Number: 4,654,363

[45] Date of Patent: Mar. 31, 1987

[54] SYNTHETIC ANALOGS OF MEVINOLIN

[75] Inventor: John D. Prugh, Chalfont, Pa.

[73] Assignee: Merck & Co., Inc., Rahway, N.J.

[21] Appl. No.: 794,890

[22] Filed: Nov. 4, 1985

[51] Int. Cl.$^4$ .................. C07D 309/30; A61K 31/365
[52] U.S. Cl. .................................... 514/460; 549/292;
514/824; 560/56; 562/466
[58] Field of Search ................ 549/292; 514/460, 510,
514/577; 560/56; 562/466

[56] References Cited

U.S. PATENT DOCUMENTS

| | | | |
|---|---|---|---|
| 4,248,889 | 3/1981 | Oka et al. | 549/292 |
| 4,255,444 | 3/1981 | Oka et al. | 549/292 |
| 4,262,013 | 4/1981 | Mistui et al. | 549/292 |
| 4,375,475 | 3/1983 | Willard et al. | 549/292 |

OTHER PUBLICATIONS

Willard et al; CA 98:17922x (1983).

Primary Examiner—Glennon H. Hollrah
Assistant Examiner—D. L. Dinner
Attorney, Agent, or Firm—Joseph F. DiPrima; Michael C. Sudol

[57] ABSTRACT

Certain 6-(substituted-naphthyl)hydrocarbyl-4-hydroxytetrahydropyran-2-ones are unexpectedly potent in the treatment of familial hypercholesterolemia, hyperlipemia and atherosclerosis by virtue of their ability to inhibit the enzyme, 3-hydroxy-3-methylglutaryl-coenzyme A reductase (HMG-CoA reductase).

8 Claims, No Drawings

SYNTHETIC ANALOGS OF MEVINOLIN

SUMMARY OF THE INVENTION

This invention relates to new compounds of structural formula:

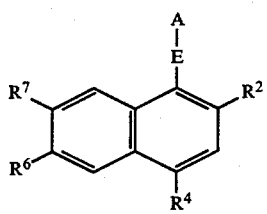

wherein A is:

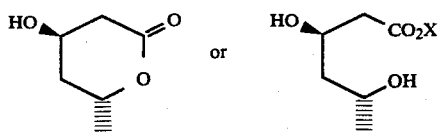

which are particularly potent inhibitors of HMG-CoA reductase and hence useful in the treatment of familial hypercholesterolemia, hyperlipemia and atherosclerosis at low doses.

BACKGROUND OF THE INVENTION

Certain natural fermentation products, notably mevinolin and compactin, and a number of semi-synthetic and totally synthetic analogs thereof are known to be inhibitors of HMG-CoA reductase and hence useful in the treatment of disease states resulting from elevated levels of serum cholesterol. In particular, U.S. Pat. No. 4,255,444 discloses compounds of formula:

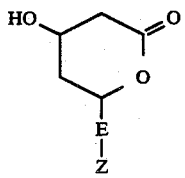

and the corresponding dihydroxy acids wherein Z is, inter alia, a naphthyl group either unsubstituted or substituted with one or more halogen atoms and/or $C_1$-$C_3$ alkyl groups, preferably chlorine or methyl groups, especially 2-methyl-1-naphthyl, but also disclosing naphthyl and 2,6-dimethylnaphthyl.

SUMMARY OF THE INVENTION

The present invention provides these novel compounds with the particular trans-stereochemical configuration in the tetrahydropyran moiety in which substantially all of the activity resides. Resolution of the trans-racemate to the 4(R),6(S)- or 4(R),6(R) enantiomer (usually dextrotatory) further optimizes activity.

Now with the present invention there are provided compounds similar to those of the prior art but with a particular pattern of trisubstitution in the naphthyl moiety (i.e., 2,4,6 or 2,4,7) whereby an unexpectedly high degree of HMG-CoA reductase inhibitory activity is achieved.

There are also provided novel processes for preparing the novel compounds; novel pharmaceutical formulations employing the novel compounds as active ingredient; and a method of treating familial hypercholesterolemia, hyperlipemia and atherosclerosis.

DETAILED DESCRIPTION OF THE INVENTION

The novel compound of this invention has structural formula (I):

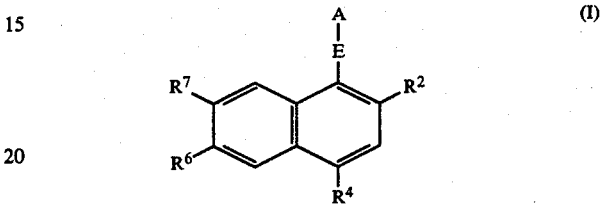

wherein A is:

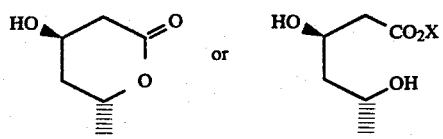

E is —$CH_2CH_2$— or —CH=CH—;

$R^2$ and $R^4$ independently are chloro, fluoro, or $C_{1-3}$ alkyl, especially methyl;

$R^6$ is hydrogen or chloro;

$R^7$ is hydrogen, chloro or fluoro provided that when $R^6$ is chloro then $R^7$ is hydrogen and when $R^6$ is hydrogen, $R^7$ is chloro or fluoro;

X is hydrogen, $C_{1-5}$ alkyl or $C_{1-5}$ alkyl substituted with a member of the group consisting of phenyl, dimethylamino or acetylamino; and pharmaceutically acceptable salts of the compounds of the formula (I) in which X is hydrogen.

One embodiment of this invention is the class of compounds of the formula I wherein $R^2$ and $R^4$ are both chloro or one is chloro and the other is methyl. A sub class of this embodiment are those compounds wherein E is —$CH_2CH_2$—. $R^6$ is hydrogen and $R^7$ is chloro or fluoro. Exemplifying this embodiment are the compounds of formula (I) having the following substitution patterns on the naphthyl moiety:

(1) 2,4,7-trichloro-1-naphthyl-;
(2) 2,4,6-trichloro-1-naphthyl-;
(3) 4,7-dichloro-2-methyl-1-naphthyl-; and
(4) 2,7-dichloro-4-methyl-1-naphthyl-.

The pharmaceutically acceptable salts of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of the formula (I) are conveniently prepared via the synthetic pathways described in Flow Sheets A & B.

Flow Sheet A
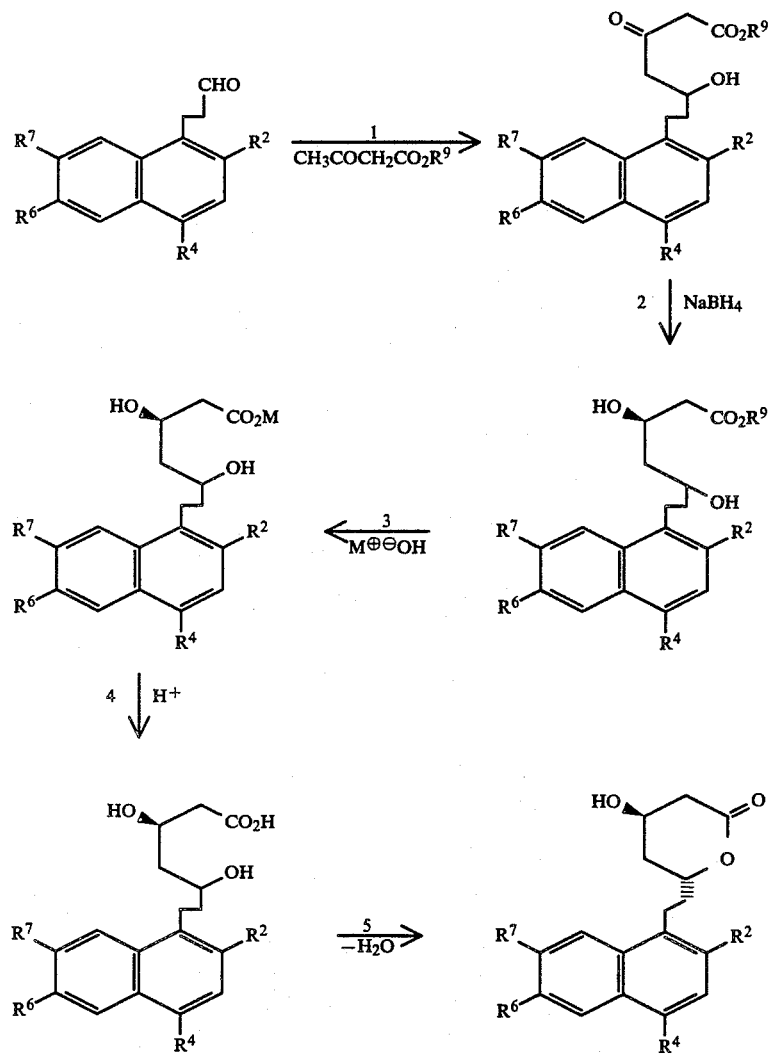
Flow Sheet B
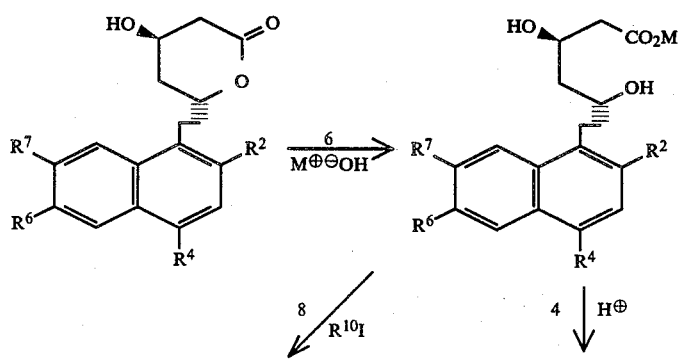

Flow Sheet B

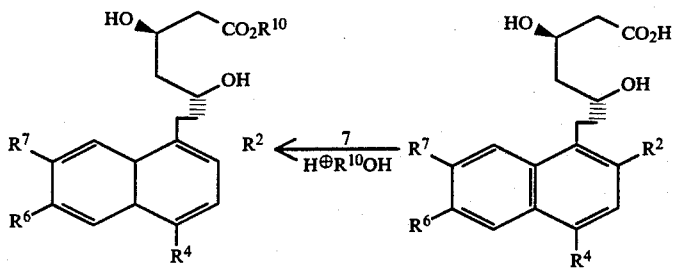

Reagents and Conditions (1) Reaction of the aldehyde with the dianion of acetoacetic ester wherein $R^9$ is $C_{1-3}$ alkyl in a suitable aprotic solvent such as THF, dioxan or the like at about $-80°$ to $-50°$ C. for 5 to 30 minutes followed by 2 to 10 hours at ambient temperature.

(2) Reduction with $NaBH_4$ in a suitable solvent such as methanol, ethanol, or the like at about $-10°$ to $+10°$ C. for about 5 to 60 minutes.

(3) Saponification of the ester with an alkali metal hydroxide, such as sodium hydroxide in aqueous alcohol.

(4) The free acids, $X=H$ are formed by treating the salts $(X=M)$ with one equivalent of a mineral acid.

(5) Lactonization by azeotropic distillation of a toluene solution.

(6) The lactone and ester, $X=R^{10}$ are saponified to form the corresponding salts, $(X=M)$ by treatment with aqueous alkali, especially an alkali metal hydroxide, preferably sodium hydroxide, or potassium hydroxide, or ammonium hydroxide.

(7) The free acids are converted to esters $(X=R^{10})$ by treatment with an alcohol of formula $R^{10}OH$ wherein $R^{10}$ is $C_{1-5}$ alkyl substituted with a member of the group consiting of phenyl, dimethylamino or acetylamino in the presence of a catalytic quantity of hydrogen ion at about 50° to about 100° C. for about 3 to 6 hours.

(8) Salts $(X=M)$ are converted to esters $(X=R^{10})$ by treatment with an alkyl halide of formula $R^{10}$ halide, preferably $R^{10}I$ in an aprotic solvent such as N,N-dimethylformamide, N-methylpyrrolidone or hexamethylphosphoramide at about 25° to 100° C. for about 18 to 36 hours.

The pharmaceutical composition of this invention comprises at least one of the novel compounds of this invention in association with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations.

A typical capsule for oral administration contains active ingredient (25 mg), lactose (75 mg) and magnesium stearate (15 mg). The mixture is passed through a 60 mesh sieve and packed into a No. 1 gelatin capsule.

A typical injectable preparation is produced by asceptically placing 25 mg of a water soluble salt of sterile active ingredient into a vial, asceptically freeze-drying and sealing. For use, the contents of the vial are mixed with 2 ml of physiological saline, to produce an injectable preparation.

The method of treating atherosclerosis, familial hypercholesterolemia, or hyperlipemia of this invention comprises administration of an effective antihypercholesterolemic amount of one of the novel compounds I to a patient in need of such treatment.

The dose to be administered depends on the unitary dose, the symptoms, and the age and the body weight of the patient. A dose for adults is preferably between 20 and 1,000 mg per day, which can be administered in a single dose or in the form of individual doses from 1–4 times per day.

The compounds of this invention also have useful antifungal activities. For example, they may be used to control strains of Penicillium sp., *Aspergillus niger*, Cladosporium sp., *Cochliobolus miyabeorus* and *Hilminthosporium cynodnotis*. For those utilities they are admixed with suitable formulating agents, powders, emulsifying agents or solvents such as aqueous ethanol and sprayed or dusted on the plants to be protected.

This invention can be illustrated by the following examples.

EXAMPLE 1

Trans-6-[2-(2,4,7-Trichloronaphalen-1-yl)ethyl]-3,4,5,6-tetrahydro-4-hydroxy-2H-pyran-2-one

Step A: Preparation of 4,6-Dichloro-7-trifluoromethanesulfonyloxyindan-1-one 4,6-Dichloro-7-hydroxyindan-1-one (21.71 g., 0.1 mole) was dissolved in DMF (80 ml) in a dry apparatus under nitrogen. Trifluormethanesulfonylchloride (21.60 g., 0.128 mole) was added with stirring, slowly, dropwise over a 20 minute period with occasional cooling to keep the internal temperature below 30° C. After the addition was complete, the reaction was stirred at room temperature for 30 minutes, then poured into ice-water with swirling. The green crystals were collected, washed with water, sucked dry, then dried in a vacuum oven at 50° C. to give 32.7 g. of the title compound mp 96°–100° C. Recrystallization from hexanes gave 22.4 g., mp 96°–98° C. A sublimed sample had mp 90°–96° C.

Calc. for $C_{10}H_5Cl_2F_3O_4S$: C, 34.40; H, 1.44; Found: C, 34.18; H, 1.37.

Step B: Preparation of 4,6-Dichloro-7-iodoindan-1-one 4,6-Dichloro-7-trifluoromethylsulfonyloxyindan-1-one (56.0 g., 0.160 mole), sodium iodide (133.1 g., 0.8 mole), and DMF (320 ml) in a dry apparatus were stirred under nitrogen at a bath temperature at 130° C. for four days, cooled to room temperature, and poured into 1 L of ice-water. The crystals were collected, washed with water, dried overnight in a vacuum oven at 50° C., then sublimed at 170°–190° C. at 0.05 mm to give 38.3 g. of crude product which was recrystalized from toluene to give 31.8 g of the title compound, mp. 170°–172° C.

pmr (DCCl$_3$): δ2.7–3.2 (4H, m), 7.6 (1H, S).

Step C: Preparation of 4,6-Dichloro-7-iodoindan-1-ol 4,6-Dichloro-7-iodoindan-1-one (14.71 g., 45 mmoles) was suspended and partially dissolved in ethanol (140 ml). Sodium borohydride (1.70 g., 45 mmoles) was added and the mixture was stirred for 50 minutes. Aqueous sodium hydroxide 20% (w/v) (40 ml) was added and stirred for 10 minutes. The reaction mixture was poured into 700 mL of ice-water with vigorous stirring. The crystals were collected, washed with water, sucked dry and dried in a vacuum oven at 50° C. overnight to give 14.08 g of the title compound, mp 95°–100° C. Recrystallization from acetonitrile gave material with mp 99°–102° C.

Calc. for C$_9$H$_7$Cl$_2$IO: C, 32.86; H, 2.14; Found: C, 33.06; H, 2.17 pmr (DCCl$_3$): δ2.1–3.3 (4H,m), 5.2 (1H,m), 7.3 (1H,S).

Step D: Preparation of 4,6-Dichloro-7-iodo-1-indene and 4,6-dichloro-7-iodo-2-indene 4,6-Dichloro-7-iodo-1-indanol (13.98 g., 42.50 mmoles) was dissolved in ether (350 ml) and the solution stirred mechanically. Phosphorus pentoxide (6.03 g. 42.50 mmoles) was added and the sealed reaction mixture was stirred vigorously overnight. The addition of phosphorus pentoxide (6.03 g., 42.5 mmoles) and stirring overnight was repeated three times. The ether containing the product was decanted, washed with aqueous NaHCO$_3$ solution, dried (MgSO$_4$), filtered, and the solvent was evaporated to leave 10.76 g. of a mixture of the title compounds, mp 89°–96° C. Recrystallization from hexane gave material with mp. 95°–97° C.

Calc. for C$_9$H$_5$Cl$_2$I: C, 34.76; H, 1.62; Found: C, 34.98; H, 1.76 pmr (DCCl$_3$): δ3.5 (2H,m), 6.5–6.9 (2H,m), 7.25 (1H, S).

Step E: Preparation of 1,1,3,5-Tetrachloro-1a,6a-dihydro-2-iodocycloprop[a]indene and 1,1,2,4-Tetrachloro-1a,6a-dihydro-5-iodocycloprop[a]indene To a solution of a mixture of 4,6-dichloro-7-iodo-1-indene, and 4,6-dichloro-7-iodo-2-indene (3.11 g., 10 mmoles) and ethyl trichoroacetate (17.2 g., 12.5 ml, 90 mmoles) in dry toluene (20 ml) cooled in an ice bath and stirred under nitrogen, was added in divided portions, fresh sodium methoxide (5.4 g., 100 mmoles). After the addition was complete, the reaction was stirred for 2.5 hours in an ice-bath. When the reaction was complete, the mixture was diluted with ether and extracted with water. The ether layer was dried (MgSO$_4$), filtered and the solvent was evaporated in vacuo to leave 8.1 g of crude product. The product was triturated with hexanes, filtered, and the solvent evaporated in vacuo from the hexane soluble product. This crude product was chromatographed on silica gel (500 g.) eluting with hexanes to give, after evaporation of the solvent, in vacuo, 1.4 g. of the mixture of compounds as an oil.

pmr(DCCl$_3$): δ2.2–2.55 (1H, m), 3.15–3.6 (3H, m), 7.2 (1H, S).

Step F: Preparation of 2,4,7-Trichloro-1-iodonaphthalene and 2,4,6-Trichloro-1-iodonaphthalene The mixture of 1,1,3,5-tetrachloro-1a,6a-dihydro-2-iodocycloprop[a]indene and 1,1,2,4-tetrachloro-1a,6a-dihydro-5-iodocycloprop[a]indene (4.54 g., 11.5 mmoles) was refluxed in 10% (w/v) KOH in ethanol (100 ml) for 1.5 hours, cooled and approximately 80% of the ethanol was evaporated in vacuo. The remainder was dissolved in ether and extracted with water, dried (MgSO$_4$), filtered, and the solvent was evaporated in vacuo to leave 3.4 g of crude product which was flash chromatographed on a silica gel column (60×150 mm) by elution with hexane to give, after evaporation of the solvent in vacuo, 2.85 g. of the product mixture mp 45°–50° C. Ratio of the two naphthalenes is 4:5 or 5:4.

pmr(DCCl$_3$): δ7.0–7.9 (4H, m).

Step G: Preparation of 2,4,6-Trichloro-1-naphthoic acid and 2,4,7-Trichloro-1-naphthoic acid (ratio 5:4 or 4:5)

The mixture of 2,4,7-trichloro-1-iodonaphthalene and 2,4,6-trichloro-1-iodonaphthalene (7.79 g. 21.8 mmoles) was dissolved in dry ether (200 ml) and cooled under nitrogen to an internal temperature of −50° C. with stirring. Butyl lithium (17.7 ml of a 1.48M solution in hexane, 26.2 mmoles) was added dropwise over about 5 minutes. The reaction was stirred for 30 minutes at −78° C. The −78° C. reaction mixture was poured onto powdered dry ice (excess) covered with ether. The excess CO$_2$ was allowed to evaporate and the ether to warm to room temperature. The ether was extracted with water once, and four times with dilute aqueous NaHCO$_3$ solution. The combined aqueous extracts were acidified with conc.HCl and the product was extracted with ether 4 times, dried (MgSO$_4$), filtered and the solvent evaporated to leave 4.0 g. of the title mixture mp 182°–200° C.

Calc. for C$_{11}$H$_5$Cl$_3$O$_2$: C, 47.95; H, 1.83; Found: C, 47.97; H, 1.88.

Step H: Preparation and separation of Methyl 2,4,6-trichloro-1-naphthoate and Methyl 2,4,7-trichloro-1-naphthoate The mixture of 2,4,6-trichloro-1-naphthoic acid and 2,4,7-trichloro-1-naphthoic acid (3.63 g., 13.2 mmoles) was dissolved in ether and cooled to 5° C. Diazomethane, in ether (generated from 3.40 g of N-nitroso-N-methylurea and base in 50 ml of ether at 5° C.) was added dropwise maintaining the internal temperature below 5° C. An excess was noted by the persistence of a yellow color. The reaction mixture was stirred a few minutes and the excess diazomethane was blown off with nitrogen and the solvent was evaporated in vacuo to leave 3.7 g of the title mixture.

The two isomers were separated by preperative HPLC (Waters 500) using 5% methylene chloride in hexane. The solvent from the first isomer to emerge from the column was evaporated in vacuo to leave 1.4 g of methyl 2,4,7-trichloro-1-naphthoate, mp 113°–115° C.

Calc. for C$_{12}$H$_7$Cl$_3$O$_4$: C, 49.78; H, 2.44. Found: C, 49.83; H, 2.38.

pmr (DCCl$_3$) δ4.09 (3H, s), 7.25–8.25 (4H, m)

The solvent containing the second isomer from the column was evaporated in vacuo to leave 1.1 g of methyl 2,4,6-trichloro-1-naphthoate, mp 110°–112° C.

Calc. for C$_{12}$H$_7$Cl$_3$O$_2$: C, 49.78; H, 2.44; Found: C, 49.86; H, 2.39.

pmr (DCCl$_3$) : δ4.07 (3Hs), 7.25–8.3 (4H, m).

Step I: Preparation of (2,4,7-Trichloronaphthalen-1-yl)methanol

A solution of methyl 2,4,7-trichloro-1-naphthoate (1.3 g, 4.5 mmoles) in ether (50 ml) was added dropwise (15 minutes) to a well stirred suspension of lithium aluminum hydride (0.25 g, 6 mmoles) in ether (25 ml). After stirring at room temperature for 17 hours the reaction mixture was treated with an additional 0.25 g of lithium aluminum hydride. The mixture was stirred for 3 hours, cooled in an ice-bath, and treated dropwise with 0.5 ml of water, 1.5 ml of 20% (w/v) of aqueous NaOH solution, and 0.5 ml of water. After filtration, the solid was extracted with ether. The combined ether solutions were dried (MgSO$_4$), filtered, and concentrated in vacuo to give 1.0 g of the title compound, mp 107°–112° C.

pmr(DCCl$_3$): δ5.23 (2H, d), 7.55–8.28 (4H, m).

Step J: Preparation of 1-Chloromethyl-2,4,7-trichloronapthalene (2,4,7-Trichloronaphthalen-1-yl)methanol (1.0 g, 3.8 mmoles) was added portionwise to thionyl chloride (10 ml) with cooling (ice bath). The reaction mixture was stirred at room temperature for 30 minutes and at reflux for 2 hours and then concentrated to dryness in vacuo. The oily residue was taken up in methylene chloride and the solution dried over MgSO$_4$. The solution was filtered and concentrated in vacuo to give 1.0 g of the title compound.

pmr(DCCl$_3$): δ5.12 (2H, s), 7.58–8.27 (4H, m).

Step K: Preparation of 3-(2,4,7-Trichloronaphthalen-1-yl)propanal

A solution of n-butyl lithium in hexane (3.2 ml, 4.3 mmoles) was added dropwise (3 minutes) to a solution of diisopropylamine (0.45 g, 4.5 mmoles) in dry tetrahydrofuran (10 ml) with cooling (ice bath). After stirring under nitrogen for 15 minutes, ethylidene cyclohexylimine (0.55 g, 4.3 mmole) was added dropwise (5 minutes) at 0° C. The mixture was stirred for 15 minutes and then the ice bath was replaced by a dry-ice-acetone bath. A solution of 1-chloromethyl-2,4,7-trichloronaphthalene (1.0 g, 3.8 mmoles) in tetrahydrofuran (15 ml) was added (5 minutes) at −75° C. The reaction mixture was stirred at −70° C. for 30 minutes and at room temperature overnight (20 hours) and then concentrated to dryness in vacuo. The residual oil was taken up in ether (100 ml) and 5% aqueous oxalic acid (100 ml) and the mixture stirred at room temperature for 3½ hours. The layers were separated and the aqueous phase extracted (2X) with ether. The ether extracts were combined, washed with cold water and brine, and dried over MgSO$_4$. The solution was filtered and concentrated in vacuo to give a red-brown oil (1.1 g). This material was chromatographed using a 50 mm flash column containing 150 g of silica gel (230–400 mesh) eluting with 30% methylene chloride in hexane (v/v) to give 0.21 g of the title compound as a pale yellow solid.

pmr(DCCl$_3$): δ2.81 (2H, m), 3.48 (2H, m), 7.53–8.27 (4H, m), 9.92 (1H, bs)

Step L: Preparation of Methyl 7-(2,4,7-trichloronapthalen-1-yl)-5-hydroxy-3-oxoheptanoate A solution of methyl acetoacetate (0.088 g, 0.76 mmole) in dry tetrahydrofuran (2 ml) was added dropwise (5 minutes) to a mixture of sodium hydride (0.036 g, 0.75 mmole) in tetrahydrofuran (3 ml) under nitrogen and with cooling (ice bath). After stirring at about 5° C. for 20 minutes, a solution of n-butyl lithium in hexane (0.55 ml, 0.77 mole) was added dropwise (5 minutes) and the mixture stirred at 5° C. for 30 minutes. The ice bath was replaced by a dry ice-acetone bath and a solution of 3-(2,4,7-trichloronaphthalen-1-yl)propanal (0.20 g, 0.7 mmole) in tetrahydrofuran (5 ml) was added (5 minutes). The reaction mixture was stirred at −70° C. for about 10 minutes and at room temperature for 5 hours and then poured into ice water containing 0.5 ml conc. HCl. After extraction with ether, the ether extracts were combined, washed with cold water and brine and dried over MgSO$_4$. The solution was filtered and concentrated in vacuo to give 0.25 g of the title compound as a yellow oil.

Step M: Preparation of Methyl 7-(2,4,7-trichloronaphthalen-1-yl)-3,5-dihydroxy heptanoate Sodium borohydride (0.02 g, 0.5 mmole) was added to a solution of methyl-7-(2,4,7-trichloronaphthalene-1-yl)-5-hydroxy-3-oxoheptanoate (0.25 g, 0.7 mmole) in ethanol (15 ml) with cooling (ice bath). The reaction mixture was stirred at about 5° C. for 30 minutes, diluted with ice and water, acidified with dilute aqueous HCl, and extracted with ether. The ether extracts were combined, washed with water and brine and dried over MgSO$_4$. The ether solution was filtered and concentrated in vacuo to give 0.22 g of the title compound as a yellow oil.

Step N: Preparation of trans-6-[2-(2,4,7-Trichloronaphthalen-1-yl)ethyl]-3,4,5,6-tetrahydro-4-hydroxy-2H-pyran-2-one A solution of potassium hydroxide (0.1 g, 1.5 mmole) in water (2 ml) was added dropwise to a solution of methyl 7-(2,4,7-trichloronaphthalene-1-yl)-3,5-dihydroxyheptanoate (0.22 g, 0.7 mmole) in methanol (10 ml) with cooling (ice bath). The bath was removed and the reaction mixture stirred at room temperature for one hour and then concentrated in vacuo. The residue was diluted with ice and water, acidified with dilute aqueous HCl and extracted with ether. The ether extracts were combined, washed with water and brine and dried over MgSO$_4$. The ether solution was filtered and concentrated in vacuo to give a yellow oil, which was taken up in toluene (75 ml). After heating at reflux for 4 hours, using a Soxhlet Apparatus containing molecular sieves, the toluene solution was concentrated in vacuo to give a viscous yellow oil (0.2 g). This material was chromatographed using a 30 mm flash column containing 50 g of silica gel (230–400 mesh) eluting with 5% acetone in methylene chloride (v/v) to give 0.035 g of the title compound as a white crystalline solid, mp 111°–115° C.

Calc. for C$_{17}$H$_{15}$Cl$_3$O$_3$: C, 54.64; H, 4.05; Found: C, 54.38; H, 4.07.

pmr(CDCl$_3$): δ1.80–2.08 (4H-m), 2.67 (1H, ddd), 2.81 (1H, dd), 3.27 (1H, m), 3.43 (1H, m), 4.44 (1H, m), 4.84 (1H, m), 7.54 (1H, dd), 7.58 (1H, s), 8.05 (1H, d), 8.21 (1H, d).

EXAMPLE 2 trans-6-[2-(1,4,6-Trichloronaphthalen-1-yl)ethyl]-3,4,5,6-tetrahydro-4-hydroxy-2H-pyran-2-one Employing the procedures substantially as described in Example 1, Steps I through N, but substituting methyl 2,4,6-trichloro-1-naphthoate for methyl 2,4,7-trichloro-1-naphthoate in Step I of Example 1 there were produced in sequence:

Step I: (2,4,6-Trichloronaphthalen-1-yl)methanol

Step J: 1-Chloromethyl-2,4,6-trichloronaphthalene

Step K: 3-(2,4,6-Trichloronaphthalen-1-yl)propanal

Calc. for $C_{13}H_9Cl_3O$: C, 54.29; H, 3.15; Found: C, 54.58; H, 3.24.

pmr(DCCl$_3$) $\delta$2.81 (2H, t), 3.50 (2H, t), 7.57 (1H, dd), 7.63 (1H, s), 7.93 (1H, d), 8.28 (1H, d), 9.91 (1H, s).

Step L: Methyl 7-(2,4,6-trichloronaphthalene-1-yl)-5-hydroxy 3-oxoheptanoate

Step M: Methyl 7-(2,4,6-trichloronaphthalene-1-yl)-3,5-dihydroxyheptanoate

Step N: trans-6-[2-(2,4,6-Trichloronaphthalene-1-yl)ethyl]-3,4,5,6-tetrahydro-4-hydroxy-2H-pyran-2-one. mp 123°–125° C.

Calc. for $C_{17}H_{15}Cl_3O_3$: C, 54.64; H, 4.05; Found: C, 54.72; H, 4.10.

prm(CDCl$_3$): $\delta$1.80–2.05 (4H, m), 2.67 (1H, ddd), 2.80 (1H, dd), 3.31 (1H, m), 3.48 (1H, m), 4.44 (1H, m), 4.83 (1H, m), 7.57 (1H, dd), 7.62 (1H, s), 8.06 (1H, d), 8.26 (1H, d).

EXAMPLE 3 trans 6-[2-(4,7-Dichloro-2-methylnaphthalen-1-yl)ethanyl]-3,4,5,6-tetrahydropyran-2-one

Step A: Preparation of Ethyl-4-chloro-2-methylphenylpropionate

Boron trifluoride etherate (1.5 ml: 0.012 mole) was added dropwise to a solution of 4chloro-2-methylphenylpropionic acid (S. Munavalli and G. Ourison, Bull. Soc. Chem. France 1964, 310) (1.99 g; 0.01 mole) in absolute ethanol (14 ml). The reaction mixture was heated at reflux for 6½ hours, cooled, concentrated in vacuo to remove the solvent and the residual oil taken up in ether. The ether solution was washed with aqueous Na$_2$CO$_3$ and cold water, dried and evaporated to give an orange oil, which was distilled at about 1.5 mm. to give the product as an oil (1.5 g, 66%), bp 126°–131° C.

Anal.: Calcd. for $C_{12}H_{15}ClO_2$: C, 63.57; H, 6.68; Found: C, 63.49; H, 6.69.

Step B: Preparation of 4-(2-Chloro-4-methyl-5'-ethoxycarbonylethyl-phenyl)-4-oxobutyric acid Aluminum chloride (5.87 g; 0.044 mole) was added portionwise (5 minutes) to a mixture of succinic anhydride (1.1 g; 0.011 mole) and 1-ethyl-4-chloro-2-methylphenylpropionate (2.27 g; 0.01 mole) in CH$_2$Cl$_2$ (20 ml) with cooling (ice bath). The reaction mixture was stirred at room temperature for 24 hours, poured into ice and 10 ml concentrated HCl and extracted with ether. The ether solution was dried and evaporated to give a yellow brown oil, which was purified by flash column chromatography (silica gel and 2% HOAc-10% acetone-90% CH$_2$Cl$_2$) to give the product as a yellow oil (3.0 g; 92% yield).

Anal. Calcd. for $C_{16}H_{19}ClO_5$: C, 58.80: H, 5.87; Found: C, 58.97; H, 6.11

Step C: Preparation of 4-(2'-Chloro-4'-methyl-5'-ethoxycarbonylethyl)-butyric acid Gaseous HCl was bubbled into a well stirred solution of 4-(2'-chloro-4'-methyl-5'-ethoxycarbonylethyl)4-oxobutyric acid (3.27 g; 0.01 mole) in acetic anhydride (60 ml) for 20 minutes with cooling (ice-acetone bath). Activated zinc dust (13.11 g 6.2 mole) was added portionwise (15 minutes) keeping the temperature below 0° C. The reaction mixture was stirred at about 0° C. for 7 hours, filtered (glass wool) into ice and water and extracted with ether. The ether solution was dried and evaporated to give a brown oil, which was purified by flash column chromatography (silica gel and 0.5% HOAc-45% acetone-95% CH$_2$Cl$_2$) to yield the product as a viscous yellow oil (2.17 g; 69%).

Anal. Calcd. for $C_{16}H_{21}ClO_4$: C, 61.43; H, 6.78; Found: C, 62.13; H, 7.48

Step D: Preparation of Ethyl 3-(4-chloro-2-methyl-8-oxo-5,6,7,8-tetrahydronaphthalen-1-yl)propanoate Oxalyl chloride (23.5 ml) was added dropwise to a well stirred solution of 4-(2'-chloro-4'-methyl-5'-ethoxycarbonylethyl)butyric acid (10.38 g; 0.033 mole) in toluene (50 ml). The reaction mixture was stirred at room temperature for 18 hours, heated at reflux for 4 hours, cooled and concentrated to dryness and the residual oil taken up in CH$_2$Cl$_2$ (50 ml). After addition of stannic chloride (31.5 ml) with cooling (ice bath), the reaction mixture was stirred at room temperature for 5 days and then poured into ice and concentrated HCl (20 ml) and extracted with ether. The ether solution was dried and evaporated to give viscous brown oil which after silica gel chromatography eluting with 15% ethyl acetate in hexane gave title compound as a gum;

$^1$HNMR (CDCl$_3$) (300 MHz): $\delta$1.27 (3H, t, CH$_2$CH$_3$) 2.10 (2H, p, CH$_2$); 2.34 (3H, s, ArCH$_3$); 2.57 (2H, t, CH$_2$); 2.65 (2H, t, CH$_2$); 2.99 (2H, t, CH$_2$); 3.21 (2H, t, CH$_2$); 4.16 (2H, q, CH$_2$CH$_3$); 7.36 (1H, s, Ar): exact mass calculated for $C_{16}H_{19}ClO_3$: 294.1021; Found: 294.1019

Step E: Preparation of Ethyl 3-(4,7-dichloro-2-methyl-8-oxo-5,6,7,8-tetrahydronaphthalen-1-yl)propanoate A solution of ethyl 3-(4-chloro-2-methyl-8-oxo-5,6,7,8-tetrahydronaphthalen-1-yl)propanoate (5.70 g, 20.3 mmoles) in CH$_2$Cl$_2$ (20 ml) was saturated with dry gaseous HCl and sulfuryl chloride (16.4 ml, 27.5 g, 203 mmoles) was added dropwise and stirred at room temperature for 2 hours. The solvent and excess sulfuryl chloride were evaporated in vacuo then chased with dry toluene two times to leave 6.40 g of title compound as a gum. Exact mass calculated for $C_{16}H_{17}O_3Cl$ (parent-HCl): 292.0866; Found: 292.0869

Step F: Preparation of Ethyl 3-(2-methyl-8-oxo-5,6,7,8-tetrahydro-4,7,7-trichloronaphthalen-1-yl)propanoate Dry HCl gas was bubbled into a solution of ethyl 3-(4,7-dichloro-7-methyl-8-oxo-5,6,7,8-tetrahydronaphthalen-1-yl)propanoate (6.40 g, 20.3 mmoles) in chloroform (20 ml). Sulfuryl chloride (16.4 ml, 27.5 g, 203 mmoles) was added. An atmosphere of HCl was generated over the reaction; it was stoppered and stirred at room temperature for 72 hours at which time tlc showed the reaction complete. The reaction was worked up by evaporating the solvent and excess sulfuryl chloride in vacuo then chased with dry toluene twice. This gave 7.38 g of title compound as a gum.

$^1$HNMR (CDCl$_3$) (300 MHz): δ1.28 (3H, t, CH$_2$CH$_3$); 2.38 (3H, s, CH$_2$); 2.61 (2H, t, CH$_2$); 2.96 (2H, t, CH$_2$); 3.17–3.24 (4H, m, CH$_2$); 4.17 (2H, q, CH$_2$CH$_3$); 7.45 (1H, s, Ar); exact mass calculated for C$_{16}$H$_{16}$Cl$_2$O$_3$ (parent-HCl): 326.0476; Found: 326.0475

Step G: Preparation of Ethyl 3-(8-hydroxy2-methyl-5,6,7,8-tetrahydro-4,7,7-trichloronaphthalen-1-yl)propanoate Sodium borohydride (0.19 g, 5.02 mmoles) was added to a solution of 3-(2-methyl-8-oxo-5,6,7,8-tetrahydro-4,7,7-trichloronaphthalen-1-yl)propanoate (7.38 g, 20.3 mmoles) in ethanol (60 ml) which had been cooled in an ice-water bath. The reaction was allowed to stir for 15 minutes. Tlc (silica-CH$_2$Cl$_2$) showed reaction not complete. Add 20 mg of sodium borohydride first stirred in the cold for 15 minutes. Repeat addition of 20 mg of sodium borohydride with 15 minutes stirring in the cold twice more at which time tlc showed reaction complete. The reaction was then partitioned between ether (150 ml) and water (300 ml). The water was extracted with ether two times. The combined ether extracts were washed with water two times, dried (MgSO$_4$), filtered, and the solvent evaporated in vacuo to leave 7.25 g of title compound as a gum.

$^1$HNMR (CDCl$_3$) (300 MHz); δ1.78 (3H, t, CH$_2$CH$_3$); 2.38 (3H, s, CH$_3$); 2.4–2.7 (2H, m, CH$_2$); 2.8–3.2 (6H, m, CH$_2$); 4.2 (2H, q, CH$_2$CH$_3$); 5.1 (1H, s, HOCH); 7.35 (1H, s, Ar). R$_f$=0.41 (2% acetone/CH$_2$Cl$_2$). Exact mass calculated for C$_{16}$H$_{18}$Cl$_2$O$_2$ (M-HOCl): 312.0684; Found: 312.0681.

Step H: Preparation of Ethyl 3-(2-methyl-4,7,7,8-tetrachloro-5,6,7,8-tetrahydronaphthalen-1-yl)propanoate Ethyl 3-(8-hydroxy-2-methyl-5,6,7,8-tetrahydro-4,7,7-trichloronaphthanalen-1-yl)propanoate (7.25 g, 19.8 mmoles) was dissolved in thionyl chloride (40 ml) and then refluxed with stirring for 2.5 hours, cooled to room temperature and the excess thionyl chloride evaporated in vacuo and chased twice with dry toluene to give 7.72 g of title compound which was used in the next step without purification.

Step I: Preparation of Ethyl 3-(4,7-dichloro-5,6-dihydro-2-methylnapthalen-1-yl)propanoate Activated zinc dust (0.55 g., 8.43 mmoles) was added to a solution of ethyl 3-(2-methyl-5,6,7,8-tetrahydro-4,7,7,8-tetrachloronaphthalen-1-yl)propanoate in dry diglyme (2.5 ml) and heated and stirred in an oil bath rapidly (10 minutes) to about 140° C. at which time the reaction proceeded vigorously and exothermically and refluxed. The reflux subsided in about 1 minute. Heating with an oil bath at 140°–150° C. was continued for 15 minutes Tlc (silica-CH$_2$Cl$_2$) showed reaction complete. The reaction was cooled to room temperature and partitioned between ether (150 ml) and 1N HCl (25 ml). Extract ether successively with 1N HCl, water four times, saturated solution of NaHCl$_3$; dried, (MgSO$_4$), filtered and the solvents evaporated to leave 1.99 g of title compound as a gum. R$_f$=0.61 (silica-CH$_2$Cl$_2$).

$^1$HNMR (CDCl$_3$) (300 MHz): δ1.29 (3H, t, CH$_2$CH$_3$); 2.28 (3H, s, CH$_3$); 2.41 (2H, q, CH$_2$); 2.62 (2H, t, CH$_2$); 2.94 (2H, q, CH$_2$); 3.04 (2H, t, CH$_2$); 4.17 (2H, q, CH$_2$CH$_3$) 6.78 (1H, t, Ar); 7.04 (1H, s, Ar); exact mass calc. for C$_{16}$H$_{18}$Cl$_2$O$_2$: 312.0684; Found: 312.0675.

Step J: Preparation of Ethyl 3-(4,7-dichloro-2-methylnaphthalen-1-yl)propanoate Ethyl 3-(4,7-dichloro-5,6-dihydro-2-methylnaphthalen-1-yl)propanoate (2.00 g, 6.39 mmoles); 2,3-dichloro-5,6-dicyano-1,4-benzoquinone (DDQ) (2.18 g, 9.58 mmoles); and dry toluene (75 ml) were mixed and heated at reflux with stirring for 2 hours. Let the reaction stand overnight when $^1$HNMR of a miniworkup showed about 3–4% unreacted starting material. Added 0.5 g of DDQ, refluxed for 2 hours; then let stand at room temperature overnight when $^1$HNMR of miniworkup showed reaction complete. Worked up reaction by filtering and wash solid with toluene. The solvent was evaporated in vacuo to leave 3.57 g of crude product which was flash chromatographed on 40×150 mm silica gel column eluting with 70% CH$_2$Cl$_2$ in hexane to give 1.78 g of title compound as an oil.

$^1$HNMR (CDCl$_3$) (300 MHz): δ1.28 (3H, t, —CH$_2$CH$_3$); 2.49 (3H, s, CH$_3$); 2.56 (2H, t, CH$_2$); 3.33 (2H, t, CH$_2$); 4.19 (2H, q, CH$_2$CH$_3$); 7.42 (1H, s, Ar); 7.47 (1H, dd, Ar); 7.99 (1H, d, Ar,); 8.20 (1H, d, Ar); exact mass calc. for C$_{16}$H$_{16}$Cl$_2$O$_2$: 310.0527; Found: 310.0527.

Step K: Preparation of 3-(4,7-Dichloro-2-methylnaphthalen-1-yl)propanal

Ethyl 3-(4,7-dichloro-2-methylnaphthalen-1-yl)propanoate (1.583 g, 5.087 mmoles) was dissolved in dry toluene (25 ml) under nitrogen with syringe cap attached to flask. The soluton was cooled to −78° C. in dry ice-acetone bath and diisobutylaluminum hydride (3.62 ml of a 1.5M solution in toluene; 5.443 mmoles) was added dropwise slowly by syringe. Stirring was continued at −78° C. for 1 hour. Then while still at −78° C., the reaction was poured quickly into an aqueous NH$_4$Cl solution with stirring. This mixture was extracted two times with ether. The combined ether extracts were extracted successively with NH$_4$Cl solution, water, brine, then dried (MgSO$_4$), filitered, and the solvent evaporated to leave a solid. This solid was triturated with a little ether in hexane to give 0.701 g of pure solid product, mp 104°–106° C. The solvent was stripped from the mother liquor to give 0.681 g of impure product. This impure product was flash chromatographed on a 20×200 mm silica column eluting with 70% CH$_2$Cl$_2$ in hexane to give 0.45 g of pure solid product mp 103°–105° C. Combining the two samples of pure solid product gave 1.15 g of pure title, compound mp 104°–106° C. after drying;

$^1$HNMR (CDCl$_3$) (300 MHz): δ2.47 (3H, s, CH$_3$); 2.76 (2H, t, CH$_2$); 3.28 (2H, t, CH$_2$); 7.42 (1H, s, Ar); 7.49 (1H, dd, Ar); 7.90 (1H, d, Ar); 8.22 (1H, d, Ar); 9.92 (1H, s, CHO); exact mass calc. for C$_{14}$H$_{12}$Cl$_2$O:

266.0265; Found: 266.0264; Anal. calc. for $C_{14}H_{12}Cl_2O$: C, 62.94; H, 4.53; Found: 63.16; H, 4.69.

Step L: Preparation of Methyl 7-(4,7-dichloro-2-methylnaphthalen-1-yl)-5-hydroxy-3-oxo-heptanoate Methyl acetoacetate (0.292 g, 2.64 mmoles) dissolved in dry THF (2 ml) is added dropwise via a syringe through a septum to a stirred suspension of sodium hydride (0.127 g of a 50% NaH in mineral oil, 2.64 mmoles) in dry THF (7 ml) which had been chilled in an ice-water bath. The reaction was stirred in the cold for 15 minutes at which time a clear solution was obtained. To this solution in the cold was added n-butyl lithium (1.80 ml of a 1.47M solution in hexane; 2.64 mmoles) via syringe through the septum dropwise in about 5 minutes. The orange solution is stirred with ice-water bath for 15 minutes and then cooled to −78° C. in a dry ice-acetone bath. To this cold stirred reaction was added dropwise via syringe, 3-(4,7-dichloro-2-methylnaphthalen-1-yl)propanal (0.6715 g, 2.513 mmoles) dissolved in dry THF (5 ml). The reaction is allowed to stir at −78° for 15 minutes, then allowed to warm to 0° by emersing the reaction flask in an ice-water bath. When ice separated from the flask, the reaction was worked up by partitioning it between ether (150 ml) and water containing 0.6 ml of 12N HCl. Extracted the water layer with ether. The combined ether extracts are washed with water twice then with saturated solution of $NaHCO_3$. The ether was dried ($MgSO_4$) and the solvent removed in vacuo to leave 0.96 g of crude title $R_f=0.45$ (silica, 5% acetone/$CH_2Cl_2$) which was used in the next step without further purification.

Step M- Preparation of Methyl 7-(4.7-dichloro-2-methylnaphthalen-1-yl)3,5-dihydroxyheptanoate A 1M solution of triethylborane (3.75 ml, 3.75 mmoles) was added to a solution of methyl 7-(4,7-dichloro-2-methylnaphthalen-1-yl)-5-hydroxy-3-oxo-heptanoate (0.96 g, 2.5 mmoles) in dry THF (9 ml). Air (7.5 ml) was bubbled slowly into the solution at room temperature with stirring. Stirring was continued at room temperature for 15 minutes then cooled in frozen methanol bath (−100° C.). Sodium borohydride (0.142 g, 3.75 mmoles) was added followed by the slow addition by syringe through a septum of methanol (2.7 ml) in about 10 minutes at −100° C. The reaction was stirred at −100° C. for 30 minutes. The frozen methanol bath was replaced by an ice-salt water bath and stirred for 10 minutes. Then added slowly a 30% solution of hydrogen peroxide (6.0 ml) dropwise so that the internal temperature does not exceed 5° C. Removed cooling bath and stirred at ambient temperature for 30 minutes. Made slightly acidic by the addition of 1N HCl then extracted with ethyl acetate three times. Washed the combined ethyl acetate extracts with water two times then brine, dried ($MgSO_4$), filtered and the solvent evaporated in vacuo to leave 0.968 g of crude product which was flash chromatographed on 50×180 mm silica column eluting with 50% ethyl acetate in hexane to give 0.476 g of title compound, exact mass calc. for $C_{18}H_{18}Cl_2O_3$ (M-$CH_3OH$): 352.0633; Found: 352.0638.

Step N: Preparation of trans 6-[2-(4,7-Dichloro-2-methylnaphthalen-1-yl)ethanyl]-3,4,5,6-tetrahydropyran-2-one Methyl 7-(4,7-dichloro-2-methylnaphthalen-1-yl)-3,5-dihydroxyheptanoate (0.476 g, 1.24 mmoles) was suspended or partially dissolved in methanol (12 ml). Sodium hydroxide solution (3.0 ml of 1N solution, 3.0 mmoles) was added and the mixture stirred until all in solution at which time tlc showed the ester hydrolyzed. The reaction was diluted with water (100 ml) and 1N HCl (3.9 ml, 3.9 mmoles) was added with swirling in a separatory funnel. The mixture was extracted with ether five times. The combined ether extracts were washed with water two times, dried ($MgSO_4$), filtered, and the solvent stripped to leave 0.418 g of acid. The acid was suspended and partially dissolved in dry toluene 240 ml and the toluene mixture refluxed and vapors returning via contact with 4A sieves in a soxhlet thimble for 6 hours when tlc showed acid converted to the lactone. The solvent was evaporated in vacuo to leave 0.405 g of crude product which was triturated with a little ether in hexane (ratio 1:4) to give 0.360 g of crystalline title compound as the 0.25 etherate, mp 111°–114° C. with partial melt and resolidity at 90°–93° C. Calc. for $C_{18}H_{18}Cl_2O_3$ $0.025C_4H_{10}O$: C, 61.36; H, 5.51; Found: C, 61.31; H, 5.64.

EXAMPLE 4

Trans-6-[2-(2,7-Dichloro-4-methylnaphthalen-1-yl)ethanyl]-3,4,5,6-tetrahydro-4-hydroxy-2H-pyran-2-one Step A: Ethyl 2-chloro-4-methylphenylpropanoate Using the procedures of Example 3, but substituting 2-chloro-4-methylphenylpropionic acid for 4-chloro-2-methylphenylpropionic acid in Step A there was obtained the title compound, bp 104°–107° C.

Anal. Calc. for $C_{12}H_{15}ClO_2$: C, 63.58; H, 6.67; Found: C, 63.25; H, 6.59

Step B: 4-[4-Chloro-2-methyl-5-(ethoxycarbonylethyl)phenyl]-4-oxobutyric acid mp 72°–74° C. Anal. Calc. for $C_{16}H_{19}ClO_5$: C, 58.81; H, 5.86; Found: C, 58.94; H, 5.88.

Step C: 4-(4-Chloro-2-methyl-5-ethoxycarbonylethylphenyl)-butyric acid mp 50°–52° C. Anal. Calc. for $C_{16}H_{21}ClO_4$: C. 61.44; H, 6.77; Found: C, 61.47; H, 6.80

Step D: Ethyl 3-(2-chloro-4-methyl-8-oxo-5,6,7,8-tetrahydronaphthalen-1-yl)propanoate mp 63°–65° C. Anal. Calc. for $C_{16}H_{19}ClO_3$: C, 65.19; H, 6.50; Found: C, 65.35; H, 6.79

Step E: Ethyl(3-(2,7-dichloro-4-methyl-8-oxo-5,6,7,8-tetrahydronaphthalen-1-yl)propanoate Step F: Ethyl 3-(4-methyl-8-oxo-5,6,7,8-tetrahydro-2,7,7-trichloronaphthalen-1-yl)propanoate mp 94°–96° C. Anal. Calc. for $C_{16}H_{17}Cl_3O_3$: C, 52.84; H, 4.71; Found: C, 52.61; H, 4.89

Step G: Ethyl 3-(8-hydroxy-4-methyl-5,6,7,8-tetrahydro-2,7,7-trichloronaphthalen-1-yl)propanoate mp 115°–117° C. Anal. Calc. for $C_{16}H_{19}Cl_3O_3$: C, 52.52; H, 5.24; Found: C, 52.91; H, 5.47

Step H: Ethyl 3-(4-methyl-2,7,7,8-tetrachloro-5,6,7,8-tetrahydronaphthalen-1-yl)propanoate recrystallization from hexane mp 92°–94° C. Anal. Calc. for $C_{16}H_{18}Cl_4O_2$: C, 50.03; H, 4.72; Found: C, 49.87; H, 4.74

Step I: Ethyl 3-(2,7-dichloro-5,6-dihydro-4-methylnaphthalen-1-yl)propanoate

Step J: Ethyl 3-(2,7-dichloro-4-methylnaphthalen-1-yl)propanoate mp 71°–73° C. Anal. Calc. for $C_{16}H_{16}Cl_2O_2$: C, 61.75; H, 5.18 Found: C, 61.71; H, 5.18

Step K: 3-(2,7-Dichloro-4-methylnaphthalen-1-yl)propanal mp 103°–105° C. Anal. Calc. for $C_{14}H_{12}Cl_2O$: C, 62.94; H, 4.53; Found: C, 62.83; H, 4.64

Step L: Methyl 7-(2,7-dichloro-4-methylnaphthalen-1-yl)-5-hydroxy-3-oxo-heptanoate

Step M: Erythro methyl 7-(2,7,dichloro-4-methylnaphthalen-1-yl)-3,5-dihydroxyheptanoate

Step N: trans-6-[2-(2,7-dichloro-4-methylnaphthalen-1-yl)ethanyl]-3,4,5,6-tetrahydropyran-2-one mp 126°–128° C. Anal. Calc. for $C_{18}H_{18}Cl_2O_3$: C, 61.20; H, 5.14; Found: C, 61.46; H, 5.18

What is claimed is:

1. A compound represented by the structural formula (I):

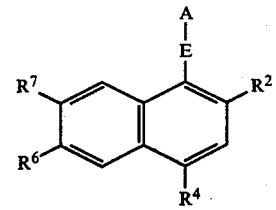

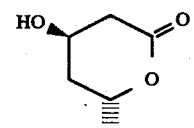

wherein A is:

E is $-CH_2CH_2-$;
$R^2$ and $R^4$ are both chloro or one of $R^2$ and $R^4$ is chloro and other is methyl;
$R^6$ is hydrogen or chloro;
$R^7$ is hydrogen, chloro or fluoro, provided that when $R^6$ is chloro, $R^7$ is hydrogen and when $R^6$ is hydrogen, $R^7$ is chloro or fluoro.

2. A compound of claim 1 which is trans-6-[2-(2,4,6-trichloronaphthalen-1-yl)ethyl]-3,4,5,6-tetrahydro-4-hydroxy-2H-pyran-2-one.

3. A compound of claim 1 wherin $R^6$ is hydrogen and $R^7$ is chloro or fluoro.

4. A compound of claim 1 which is trans-6-[2-(2,4,7,-trichloronaphthalen-1-yl)ethyl]-3,4,5,6,-tetrahydro-4-hydroxy-2H-pyran-2-one.

5. A compound of claim 1 which is trans-6-[2-(4,7-dichloro-2-methylnaphthalen-1-yl)ethyl]-3,4,5,6-tetrahydro-4-hydroxy-2H-pyran-2-one.

6. A compound of claim 1 which is trans-6-[2-(2,7-dichloro-4-methylnaphthalen-1-yl)ethyl]-3,4,5,6-tetrahydro-4-hydroxy-2H-pyran-2-one.

7. A hypocholesterolemic, hypolipidemic pharmaceutical composition comprising a nontoxic therapeutically effective amount of a compound of claim 1 and a pharmaceutically acceptable carrier.

8. A method of inhibiting cholesterol biosynthesis comprising the administration to a subject in need of such treatment a therapeutically effective amount of a compound of claim 1.

* * * * *